tle=US007454322B2

United States Patent
Carpentier et al.

(10) Patent No.: US 7,454,322 B2
(45) Date of Patent: Nov. 18, 2008

(54) METHOD FOR MODELING HYDROCARBON DEGRADATION IN AN OIL DEPOSIT

(75) Inventors: Bernard Carpentier, Labbeville (FR); Ludovic Martin, Bobigny (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 220 days.

(21) Appl. No.: 10/491,688
(22) PCT Filed: Oct. 3, 2002
(86) PCT No.: PCT/FR02/03387

§ 371 (c)(1),
(2), (4) Date: Sep. 9, 2004

(87) PCT Pub. No.: WO03/031644

PCT Pub. Date: Apr. 17, 2003

(65) Prior Publication Data

US 2005/0015228 A1 Jan. 20, 2005

(30) Foreign Application Priority Data

Oct. 5, 2001 (FR) ................................. 01 12892

(51) Int. Cl.
| | |
|---|---|
| G06G 7/48 | (2006.01) |
| G06G 7/50 | (2006.01) |
| G06G 7/58 | (2006.01) |
| C09K 8/68 | (2006.01) |
| C02F 3/34 | (2006.01) |
| C02F 3/00 | (2006.01) |
| A62D 3/00 | (2007.01) |
| A62D 3/02 | (2007.01) |
| B09B 3/00 | (2006.01) |
| B09C 1/10 | (2006.01) |

(52) U.S. Cl. .............................. 703/10; 703/9; 703/11; 703/12; 507/200; 507/201; 435/262; 435/262.5; 435/264; 435/281

(58) Field of Classification Search ............... 703/9–12; 210/170.01, 170.07; 507/200–201; 702/6–13; 435/262, 262.5, 264, 281

See application file for complete search history.

(56) References Cited

U.S. PATENT DOCUMENTS 6,151,566 A * 11/2000 Whiffen ...................... 703/10

(Continued)

OTHER PUBLICATIONS

Larter et al. "Biodegration rates assessed geologically in a heavy oil field, implecations for the deep slow (Largo) biosphere Phenix Goldschimdt" Heavy Oilfield Biosphere, 2000, pp. 1-4.*

(Continued)

*Primary Examiner*—Kamini Shah
*Assistant Examiner*—Suzanne Lo
(74) *Attorney, Agent, or Firm*—Antonelli, Terry, Stout & Kraus, LLP.

(57) ABSTRACT

Method of modeling the biodegradation of hydrocarbons trapped in an oil reservoir or trap through the action of the bacterial population in an underlying aquifer.

From data relative to the reservoir studied, concerning the form and the height of the reservoir, the physical characteristics of the porous medium, the thickness of the transition zone between the hydrocarbons and the water, the composition of the hydrocarbons, of the flow of electron acceptors entering the reservoir and data relative to the bacterial population in the aquifer, modeling is performed by discretizing the reservoir by means of a grid wherein the height of each grid cell is the thickness of the transition zone, and the variation, over the height of the reservoir, of the proportion in heavy fractions of hydrocarbons under the effect of the biodegradation is determined by iterative adjustment in each grid cell of the bacterial population to the amount of hydrocarbons available, the pore space available, the amount of electron acceptors present in the reservoir and the degradation capacities of said population.

Applications: determination of the composition of oils in a reservoir and notably of the location of the heaviest fractions.

4 Claims, 5 Drawing Sheets

U.S. PATENT DOCUMENTS 6,766,817 B2    7/2004   deSilva
2006/0020438 A1*  1/2006   Huh et al. .................... 703/10

OTHER PUBLICATIONS

Lu et al. "Natural Attenuation of BTEX Compounds: Model Development and Field-Scale Application" vol. 37, No. 5, Ground Water Sep.-Oct. 1999 pp. 707-717.*

Carpentier, Bernard. "New Concepts for Biodegration Evaluation in Oil fields, a Combined Geological and Numberical Approach", Mar. 10-13, 2002. AAPG Annual Meeting, 1 page.*

Essaid et al. "BIOMOC, A Multispecies Solute-Transport Model with Biodegration" 1997, U.S. Geological Survey, Water-Resources Investigations Report 97-4022. 77 pages.*

Eganhouse et al. "Processes Affecting the Fate of Monoaromatic Hydrocarbons in an Aquifer Contaminated by Crude Oil", Environmental Science & Technology, 1996, vol. 30, No. 11, pp. 3304-3312.*

Schaerlaekens et al. "Numerical simulation of transport and sequential biodegration of chlorinated aliphatic hydrocarbons using CHAIN_2D", Hydrological Processes, 1999, vol. 13, pp. 2847-2859.*

Delin et al. "Ground Water Contamination by Crude Oil near Bemidji, Minnesota", Sep. 1998, USGS, 4 pages.*

G. Lu et al. Natural Attenuation of BTEX Compounds: Model Development and Field-Scale Application vol. 37. No. 5-Ground Water Sep.-Oct. 1999 pp. 707-717.

I. Cozzarelli, et al "Geochemical heterogeneity of a gasoline-contaminated aquifer", pp. 261-284, 1995.

K. Pecher, et al Reductive Dehalogenation of Chlorinated Hydrocarbons during Anaerobic Stabilization of Municiple Wastes, pp. 271-279, 1999.

* cited by examiner

Grid cell représenting the water/oil transition zone

Oil flow filling the réservoir

Electron acceptor flow carried by the aquifer

Grid cell représenting the water/oil transition zone

Electron acceptor flow carried by the aquifer

1 Grid cell $S_{moy}$ $S_{oil}$

Thickness of the water/oil transition zone

\* form factor

Nomber of bacteria as a function of geometric conditions of the medium and saturation

METHOD FOR MODELING HYDROCARBON DEGRADATION IN AN OIL DEPOSIT

FIELD OF THE INVENTION

The present invention relates to a method of modeling the biodegradation of hydrocarbons trapped in an oil reservoir or trap, through the action of the bacterial population in an aquifer, from data relative to the reservoir studied.

The method according to the invention allows to form an assessment tool particularly useful notably to geologists anxious to direct investigations out of risk areas.

BACKGROUND OF THE INVENTION

Biodegradation of an oil is an alteration phenomenon caused by the oxidation of certain hydrocarbon molecules by micro-organisms or bacterial flora, which leads to the formation of a heavy oil, therefore difficult to produce and not very cost-effective commercially. The bacteria consume these molecules as they respire and to get the elements essential for their growth and their replication. The study of this phenomenon arouses renewed interest with the development of deep-sea exploration, the presence of heavy oil being a major risk. There are not many means currently available to predict biodegradation risks and to describe this phenomenon, whereas the economic need for the development of quantitative tools is great nowadays.

Biodegradation is a bio-geochemical process similar to a cold combustion performed by micro-organisms. A bacterium capable of degrading hydrocarbon compounds can in fact be considered as a hydrocarbon-consuming machine using electron acceptor ions (that can be compared to an oxidizer) and rejecting reducers.

A first condition for the existence of biodegradation is naturally the existence of these microorganisms. They are present in the medium either since the deposition of the sediment layer at the surface or because they have been brought there by meteoric water. In the absence of petroleum organic matter or of other sources of carbon ($CO_2$, carbonate ions, etc.), the bacteria encyst and can be preserved during very long periods of time.

It is well-known that there are two distinct bacterial mechanisms causing the degradation of organic matter:

Catabolism, also referred to as respiration. It is the process of decomposition of the organic matter by oxidation in order to supply energy stored in the ATP (adenosine triphosphate) molecules. It requires organic matter and electron acceptor (not necessarily oxygen). The chemical balance is not yet well known and changes for each hydrocarbon molecule.

Anabolism. It is the process of formation of cellular matter allowing bacterial replication and growth. The bacterium needs all the constituent elements thereof, mainly C, O, N, S, K, P. Knowledge of the proportions of each of these elements in a bacterium would give a first balance of their relative consumption in the medium. Anabolism uses the energy supplied by respiration to effect its chemical reactions. The global chemical balance of a bacterium effecting its anabolism is thus a combination of the one related to the creation of cellular matter and of respiration.

Respiration is a permanent process whereas anabolism occurs only at certain points in the life of the bacterium. Only respiration has been studied because it is considered to be preponderant over anabolism in the degradation of hydrocarbons. However, the two mechanisms are not independent. When a bacterium effects its anabolic process, it increases its respiration because it needs much energy.

The table hereafter gives examples of electron sources and acceptors, and of products of the reactions that can be observed in oil reservoirs.

| Electron acceptors | Electron sources | Products |
| --- | --- | --- |
| $O_2$ | HC | $CO_2$ |
| $MnO_2$ | HC, H+ | $CO_2$, $Mn^{2+}$ |
| $NO_3^-$ | HC, H+ | $CO_2$, $N_2$ |
| $Fe(OH)_3$ | HC, H+ | $CO_2$, $Fe^{2+}$ |
| $SO_4^{2-}$ | HC, HC+ | $CO_2$, $H_2S$ |
| Possible $CO_2$ | HC | $CO_2$, $CH_4$ |

A known biodegradation model of a field from data from the Gullfaks field in the North Sea is described in the following publication:

Horstad I., Larter S. R., Mills N., A quantitative model of biological petroleum degradation within the Brent group reservoir, Org. Geochem., 19, pp. 107-117.

According to this model, filling of a trap with hydrocarbons is considered with a constant flow. Water saturated with electron acceptors also circulates with a constant flow. The field has a simple parallelepipedic symmetry. During filling in the transition zone, the destruction of four n-alkanes is calculated by means of conventional kinetic laws of the first order obtained in the laboratory. The equational balance consists of a kinetic term of hydrocarbon destruction and the terms of hydrocarbon and electron acceptor supply by convection. The degradation is double, aerobic and by sulfate reduction.

In this system, the electron acceptor supply is the limiting factor. The parameters controlling the system are the thickness of the transition zone, the flow rate of water under the transition zone. The results obtained by this type of model are not really realistic. This is due to the balances and to the reaction kinetics selected, the latter being linked with the lack of knowledge about the bacterial kinetics and the attack mechanisms developed by the bacteria.

Models involving a more complex approach of the porous medium and of matter transport are commonly used to simulate biodegradation in shallow polluted layers. The SIMUSCOP model is notably used, which allows 2D-gridding of a subsoil and calculation of the aerobic biodegradation on the BTEX, developed by the applicant, on the basis of the work described in the publication hereafter:

Côme J. M., Expérimentation et modélisation de procédés in situ de dépollution par biodégradation aérobie des aquifères contaminés par des hydrocarbures, mémoire de thèse, pp. 75-93, April 95.

The softwares BIO1D, developed by the ECHOSCAN company, RT3D or PARSSIM1 (Texas University) can also be mentioned. Documentation relative to these models is available at the following Internet addresses:

Model BIO1D: http://people.becon.org/~echoscan/13-22 htm

Model PARSSIM: http://king.ticam.utexas.edu/Groups/SubSurfMod/ColorPictures/caption.html Model RT3D: http://bioprocess.pnl.gov/rt3d_descrip.htm.

A bibliography concerning the simulation of biodegradation within the framework of depollution is also available at the following address:

http://www.nal.usda.gov/wqic/Bibliographies/qb9406.html.

In most of these models, only the hydrocarbon molecules with a high solubility in water (BTEX) are considered. Oil is therefore present in the dissolved form and moves only by diffusion. Sometimes, residual oil moving by convection is also taken into account. Although the oil saturations involved are not the same as in an oil reservoir and emphasis is put on matter transport in the aquifer, the mathematical problematics is in fact applicable to reservoirs.

The equations used in all these models are of the form as follows:

$$\frac{\partial c_\alpha}{\partial t} = \frac{\partial}{\partial xi}\left(Vc_\alpha - D\frac{\partial c_\alpha}{\partial xi}\right) + q_\alpha c_\alpha \quad (1)$$

In this equation, where $$\frac{\partial c\alpha}{\partial t}$$

is an accumulation term, $Vc_\alpha$ is a transport term, $$D\frac{\partial c\alpha}{\partial xi}$$

is a reaction term of the $1^{st}$ order and $q_\alpha c_\alpha$ is a source term,
T is time,
xi is a space variable at x, y and z,
P is the number of chemical species,
V(xi,t) is the velocity field of a fluid (water),
D(xi,t) is the diffusion coefficient,
$c_\alpha$ is the concentration of species $\alpha$, and
$q_\alpha$ is the kinetic reaction coefficient of the $1^{st}$ order of species $\alpha$.

The problem is completed by means of a certain number of initial conditions and of boundary conditions such as the initial concentrations, the diffusion source zones, the impossible transport zones, etc.

In order to describe a geologic porous medium, 3D models have been developed wherein an aquifer zone is gridded, and the velocity fields and the concentrations are determined in each grid cell.

All these models provide a very realistic description of the geologic medium, but they only take into account oils whose composition is not very elaborate, limited to some molecules among the most soluble ones or even to a single type hydrocarbon molecule. These models are therefore not usable per se for modeling biodegradation in reservoirs in order to obtain a description of the evolution of oil. Furthermore, for an application to geologic time scales, the problem remains the type of kinetics applied for biodegradation reactions.

SUMMARY OF THE INVENTION

The method according to the invention allows to model the progressive biodegradation of hydrocarbons trapped in an oil reservoir or trap studied, through the action of a bacterial population in an aquifer, from data relative to the reservoir studied, concerning the form and the height of the reservoir, the physical characteristics of the porous medium, the thickness of the transition zone between the hydrocarbons and the water, the composition of the hydrocarbons, of the flow of electron acceptors entering the reservoir and data relative to the bacterial population in the aquifer, in order to determine the development conditions of the reservoir.

It is characterized in that it comprises:
discretizing the reservoir by means of a grid wherein the height of each grid cell is the thickness of the transition zone, and
determining the variation, over the height of said reservoir, of the proportion in heavy fractions of hydrocarbons under the effect of biodegradation by progressive adjustment in each grid cell of the bacterial population to the the amount of hydrocarbons available, to the pore space available, to the amount of electron acceptors present in the reservoir and the degradation capacities of said population.

According to an implementation mode, the initial hydrocarbon filling rate of the reservoir when the temperature conditions prevailing in the reservoir lend themselves to biodegradation is first determined.

By taking account of the long-term effects of the biodegradation of oils in a reservoir, the method allows to obtain much more realistic assessments than with prior methods of the distribution of the hydrocarbon constituent fractions and to better select the reservoir development zones.

BRIEF DESCRIPTION OF THE FIGURES

Other features and advantages of the method according to the invention will be clear from reading the description hereafter of non-limitative examples, with reference to the accompanying drawings wherein.

DETAILED DESCRIPTION

The model takes account of an oil composition comprising eight compound classes. Each compound class is associated with a stoichiometric balance and a preference factor; simulation thus allows to follow the evolution of the oil composition.

It uses a biodegradation kinetics involving bacteria attack mechanisms in the porous medium.

1.1.1 The Model

The tool for implementing the model is for example a known software platform called FLUID FOLDER, suited for fast simulation of traps, fluids and alteration phenomena: mixing, leaching, phase change, thermal cracking, etc.

Figure 1A:
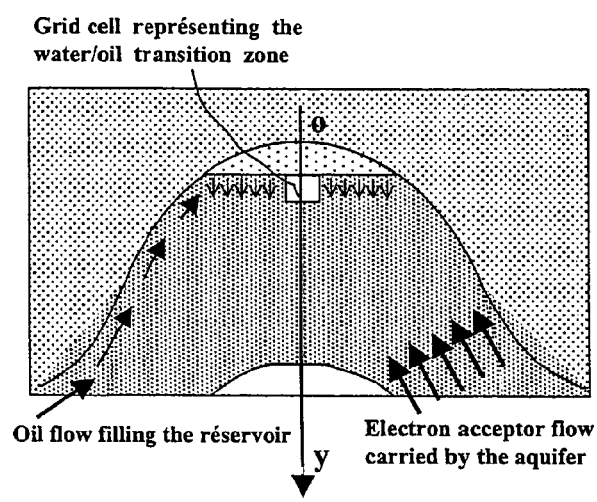
FIG. 1a diagrammatically shows, in a geologic trap under filling, the displacement of a water/hydrocarbon transition zone, biodegradation occurring in the transition zone which moves downwards as the field fills up, a case where all of the oil may be totally degraded, FIG. 1b diagrammatically shows another situation where biodegradation occurs only after filling of the trap, in the water/hydrocarbon transition zone located at the base of the reservoir; the biodegradation <<rises>> slowly in the reservoir and affects only the basal part of the reservoir, FIG. 2 diagrammatically shows the water/hydrocarbon transition zone inside a grid cell of the trap discretized by means of a grid pattern, FIGS. 3a, 3b diagrammatically show respectively a <<real>> porous medium and the simplified porous medium wherein, for calculation of the water/oil contact surface at the pore scale, the oil present in the pore is represented by a single sphere whose volume is in accordance with the oil saturation of the pore.
Figure 1B:
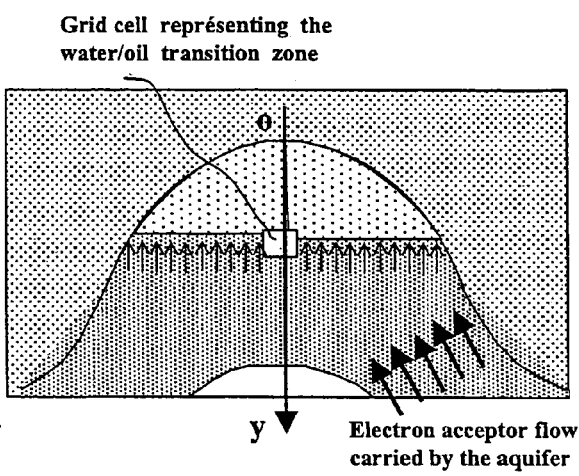
Figure 2:
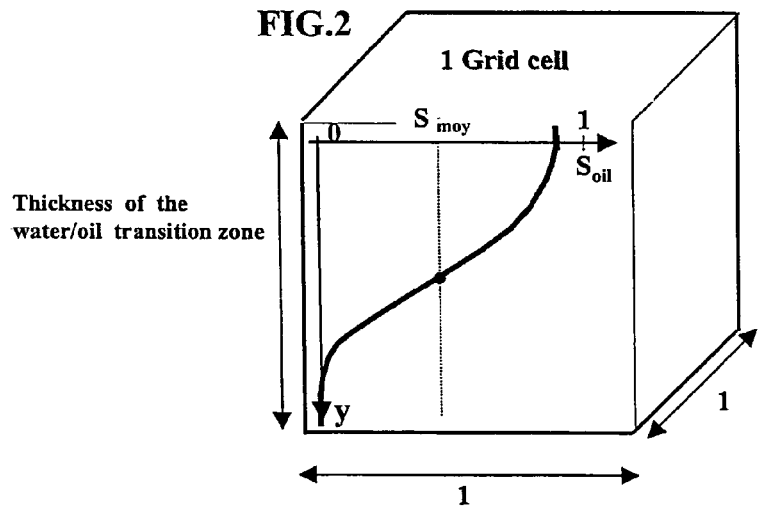

In this model, we consider a trap (porous zone with a curved geometry allowing oil accumulation) that is discretized by means of a grid pattern. The fluid is biodegraded in a grid cell located near to the water/oil transition zone of the reservoir (FIGS. 1a, 1b). Each grid cell is a parallelepiped whose base has a 1-unit surface area and whose height is the thickness of the water/oil transition zone accessible by the bacteria. In each grid cell (FIG. 2), the oil is at a variable saturation, from the base of the zone containing only water to the top of the cell which contains a residual amount of water, greater than or equal to the irreducible saturation of the order of 20%. To simplify calculation, an average global saturation is taken into account in the cell.

The quantities associated with the grid cell are:
a biodegradation time,
a global oil saturation,
an oil composition (for the moment 8 compound classes),
a bacterial population

1.1.1.1 Description of the Trap

The following quantities are associated with the porous zone:
The geometry of the trap, for example the height and the surface forming the top of the trap. It is known from seismic images obtained during a seismic prospecting survey in the basin.
The characteristics of the porous medium (porosity, pore size, etc.). If the geologic trap studied has not been drilled yet, they can be evaluated when the type of sedimentary deposits obtained from prior regional geologic studies is known. These are generally sensitive parameters which influence the amount of hydrocarbons in place. The model allows to test the influence of these parameters on the oil in place. If exploratory drilling has already been carried out through the geologic trap, the characteristics of the porous medium are known from the result of logging or coring operations.
The hydrocarbon flow and its variation with time. It is known or estimated using a known basin modeling tool such as TEMIS for example.
The thickness of the transition zone. If the trap has not yet been drilled, the thickness of this zone is deduced from relations known to specialists which connect the capillary pressure and the thickness of the transition zone.
The composition of the oil. If no in-situ measurements are available, the composition used is the one obtained by using a known basin composition modeling tool such as TEMISCOMP for example, or the composition of an oil belonging to the same petroleum system, but not degraded. A composition with eight compound classes for example is taken into account.
The electron acceptor flow and its variation with time. The flow of water in the trap is also the result of modeling using a basin model. If the trap studied has not been drilled, the composition of the water considered is that of a known zone of the sedimentary basin in which the trap lies. The composition of the water can also be obtained using a known diagenesis simulation tool such as DIAPHORE for example. If the trap has already been drilled, the water composition selected is a priori the current composition of the aquifer.
General data relative to the adaptation of the bacteria to the medium corresponding to the reservoir: average size of a bacterium, electron acceptor consumption rate, absolute preference factors for the various molecule classes. If the trap has not been drilled yet, known results obtained in the laboratory are used. If the trap has already been drilled down to the aquifer, bacteriological measurements (very slow under anaerobic conditions) are performed on the water in its current state.

Two possible geologic scenarios have been studied in this trap to model biodegradation:

1.1.1.1.1 The Equations Hereafter, Which Govern These Quantities in the Grid Cell, Are:

a) the material balance equations which govern the grid cell:
the oil balance equation taking account of the oil which supplies the cell by convection and of the oil eliminated by the biodegradation reaction,
the balance equation of the electron acceptor which supplies the cell by diffusion and convection, and is eliminated by biodegradation; the biodegradation is controlled by the rate of consumption of the bacterial population,
the equation which governs the bacterial population; this population is adjusted as a function of the water/oil interface, of the volume available and of the amount of electron acceptors.

$$\frac{dC_1}{dt} = \left(\frac{dC_1}{dt}\right)_{convection} - X_{rel\_i}(C_i) \cdot stoichio(i) \cdot \frac{d[Acc]}{dt}, \quad (2)$$

$$\frac{d[Acc]}{dt} = \left(\frac{d[Acc]}{dt}\right)_{diffusion} + \left(\frac{d[Acc]}{dt}\right)_{convection} - Fa\left(\frac{dB}{dt}\right), \quad (3)$$

$$\frac{dB}{dt} = f\left(\sum_j C_j\right) - Fb\left(\frac{d[Acc]}{dt}\right) \quad (4)$$

In these equations,
[Acc] is the electron acceptor mass concentration,
[$C_i$] the hydrocarbon i mass concentration,
B the bacterial population (in units/ml),
stoichio(i) the stoichiometric biodegradation coefficient in the reaction involving hydrocarbon i:

Hydrocarbon i+stoichio(i) [Acc]−>products

Xrel_i the relative preference factor of hydrocarbon i.

$$Fa\left(\frac{dB}{dt}\right) = Kcin\frac{dB}{dt}$$

kinetic function of the first order depending on the bacterial population and corresponding to its respiration.

$$Fb\left(\frac{d[\text{Acc}]}{dt}\right) = \begin{cases} 0 & \text{if there are more electron acceptors than needed by the bacteria} \\ \frac{1}{K_{cin}} \frac{d[\text{Acc}]}{dt} & \text{otherwise} \end{cases}$$

$$f\left(\sum_j C_j\right)$$

represents the number of bacteria required to cover the interface of a monolayer within the limits of the space available (at least 20% of free pore volume must remain).

1.1.1.1.2 The Compound Classes and Their Preference Coefficients

The compound classes selected to represent the oil are deduced from Peters and Moldowan's biodegradation advancement scales which correspond to the present state of knowledge of the preference factors, as defined in the following publication for example:

Peters K. E. and Moldowan J. M., "The Biomarker Guide", Ed. Printice Hall, 1993.

These classes are as follows, in order of attack preference:
1—C6–
2—N-paraffins C6-C15
3—Isoparaffins C6-C15
4—Isoprenoids C6-C15
5—Naphthenes C6-C15
6—Aromatics C6-C15
7—Saturates C15+
8—Aromatics C15+.

Each compound class is assigned an absolute and relative preference coefficient.

The absolute preference coefficient is the amount (in relation to the total oil) of this consumed compound class if the bacteria are placed in a situation where they have equal access to each compound class. This coefficient expresses an attraction in the absolute of the bacteria for the various compound classes.

The relative preference coefficient of a compound class i is deduced from the absolute coefficient weighted by the compound class content.

$$X_{\text{rel\_i}} = \frac{X_{\text{abs\_i}} \cdot [C_i]}{\text{number of compound classes}}$$

where $X_{abs\_i}$ is the absolute preference factor for hydrocarbon i.

1.1.1.1.3 Biochemical Kinetics

By first hypothesis, the bacteria function only under respiration conditions. This means that the growth stage of the bacterial population in terms of biodegradation and of amount of reactants involved in this growth stage is disregarded in this model. The system is brought back to a stable bacterial population at each calculation step which regenerates by itself and which, globally with the outside environment, behaves as a simple system that respires.

As mentioned above, the model also takes account of a biodegradation kinetics which is a function of the bacterial population and not only of the reactants according to Monod's law notably. The biochemical kinetics no longer depends only on the amount of reactants provided by the geologic environment. The bacterial population influences the amount of reactants involved.

In order to take this kinetics into account, the amount of electron acceptors involved in the biodegradation, which is a function of the bacterial population, is calculated. If the geologically imported amount is overabundant in relation to the maximum bacterial population, only part of this amount is effectively consumed; otherwise, it is considered to be entirely consumed. A first order type law is then applied.

Calculation of the Bacterial Population

As already mentioned, the bacteria tend to join together into biological flocs and to increase the surface area of the water/oil interface. For simplification reasons, it is assumed that these mechanisms are limited by the available volume, the porosity decreasing with the depth. One considers that the bacterial population occupies, on the scale of the droplets in the porous medium, the water/oil interface of a monolayer.

Figure 3A:
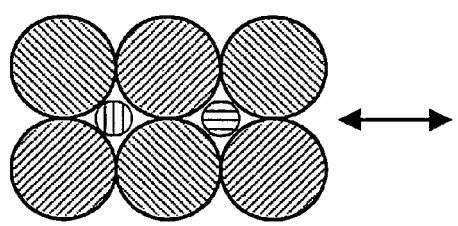
Figure 3B:
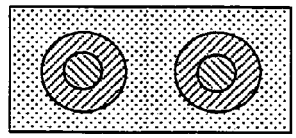

To calculate the bacterial population, the porous medium is represented by an equivalent medium that is geometrically simpler (FIGS. 3a, 3b). Each porous interstice is reduced to a spherical cavity. In each porous interstice, the oil at the current saturation is gathered into a spherical drop. The maximum number $N_b$ of bacteria that can cover this surface area is calculated, knowing that the specific surface $A_b$ of each bacterium that can cover the droplet is:

$N_b$=Interface/$A_b$, where $A_b = \pi . R_b^2$, with $R_b$: mean radius of a bacterium.

This number of bacteria obtained then has to be adjusted according to two criteria:

1) The remaining free pore space (once the volume occupied by the oil and the bacterial population counted) must be greater than 20%.

If the free pore space is below 20%, the population is adjusted so that the free pore space reaches 20% (20% is a "reasonable" arbitrary value allowing a certain bacteria mobility). In this case, this means that the bacterial population is not sufficient in number to cover all of the interface. Part of the molecules is then dissolved in the aquifer and it is also to the advantage of the bacteria to occupy the aquifer to catch these molecules.

Figure 4:
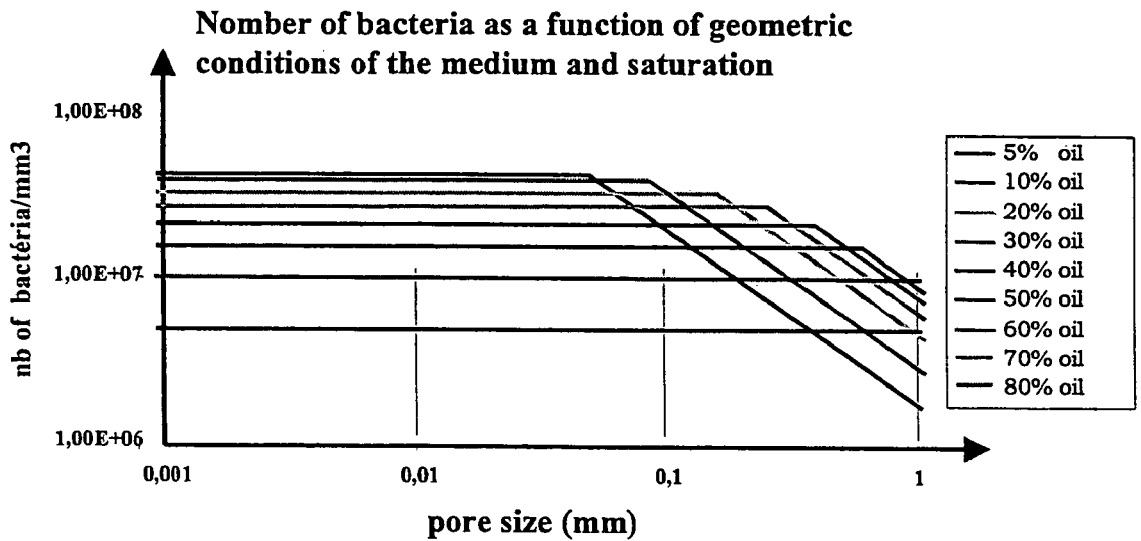
FIG. 4 shows an example of bacterial population evolution calculated by the model as a function of the pore sizes in a porous medium containing oil at different saturations.
Figure 5:
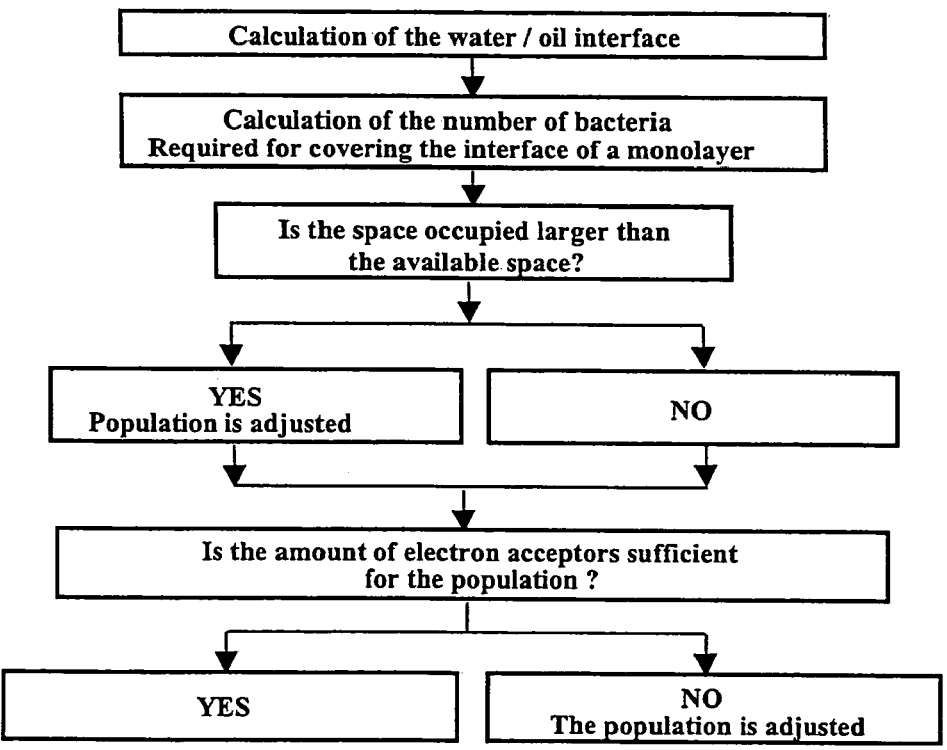
FIG. 5 shows an example of a logic flowchart for calculation of the bacterial population, which is adjusted so as to be compatible with the petrophysical parameters (pore volume, saturation . . . ) and the amount of electron acceptors present in the grid cell at a time T.

FIG. 4 illustrates an application example where the bacterial population has been determined as described above for bacteria having a mean radius of 1 micron. The population is calculated with a variable porosity and a variable oil saturation. The slope lines correspond to a population which needs no correction, the free space being above 20%. The horizontal lines represent a population that has been adjusted so as to obtain a 20% porosity. It can be observed that a minimum pore size of the order of 100 microns and a rather low oil saturation are required to hope of a complete interface cover.

2) The electron acceptor requirements of the bacteria during the time associated with the grid cell must be less than or equal to the amount of electron acceptors supplied.

If the amount of electron acceptors supplied by the aquifer is less than the amount required for the survival of all of the population compatible with the amount of hydrocarbons, the bacterial population will decrease within a very short period of time (a single generation of several hours must be sufficient in practice) so as to adjust to the amount of electron acceptors available. In this case, and in this case only, this means that, in the end, we come back to a system whose kinetics is controlled by the electron acceptor supply, and the equation balances can be written directly with a Monod type law well-known to specialists, which connects the bacterial growth rate to the amount of biomass present.

Thus, this model develops a new approach which takes account of the strategies of oil attack by the bacteria and of the bacterial population present to control the reaction kinetics.

Calculation of the Amount of Oil and of Electron Acceptors Supplied by Convection In the model, convection is a constant-flow phenomenon for a cell of the vertical grid pattern, but it can be variable during filling of the next cell located below. Because of the geometry of the trap, if the flow remains constant during filling of several consecutive grid cells, the amount of oil and of electron acceptors in the cells will be variable.

The quantity used for the oil is the yearly volume entering the trap. This quantity is to be divided by the number of grid cells that can be arranged laterally in the transition zone, a quantity that is variable as a function of the geometry of the trap, in order to obtain the amount of oil filling a single cell at each unit of time.

In the simulations performed, the value of the reference case taken for this flow is 1.4 l/year; this allows filling of the Gaussian trap of height 100 m and width 2000 m in 100 000 years. For the electron acceptors, the quantity used is the mass of electron acceptors flowing through 1 ml water in one year in the aquifer.

In the simulations carried out for the type case, a 25 ppm/ml water electron acceptor saturation has been considered. If one considers only oxygen of molar mass 16 g/mol, this means, for an aquifer moving by 1 cm/year, a flow of 2 mg/ml water/year.

Calculation of the Amount of Electron Acceptors Diffused

The diffusion occurs vertically from the water column considered as an infinite medium of constant electron acceptor concentration to the transition zone. The diffusion creates a concentration gradient in the transition zone. To simplify, an average concentration is calculated for all of the transition zone.

Such a system is governed by Fick's law; the balance equation is thus:

$$\frac{\partial C}{\partial t}(z, t) = K \frac{2\Phi}{3-\Phi} \frac{\partial^2 C}{\partial z^2}(z, t)$$

where K is the diffusion coefficient and $$\frac{2\Phi}{3-\Phi}$$

represents the tortuosity (porosity).

The solution of this equation gives:

$$\frac{C(z, t) - C0}{C(z, 0) - C0} = \operatorname{erf} \frac{z}{2\left(\frac{2\Phi}{3-\Phi} Kt\right)^{1/2}}$$

$$\frac{C(z, t) - C0}{C(z, 0) - C0} = \operatorname{erf} \frac{z}{2\left(\frac{2\Phi}{3-\Phi} Kt\right)^{1/2}} \text{ with } \operatorname{erf}(u) = \frac{2}{\sqrt{u}} \int_0^u e^{-x^2} dx$$

Calculation of the average value of concentration C gives:

$$\overline{C} = \frac{1}{L} \int_0^L C(z, t) dx.$$

Reservoir Filling Scenarios

Two scenarios are possible according to whether the accumulation of oil in the trap has occurred under favourable conditions (notably a compatible temperature) or not as regards biodegradation phenomena.

Scenario 1

Figure 6:
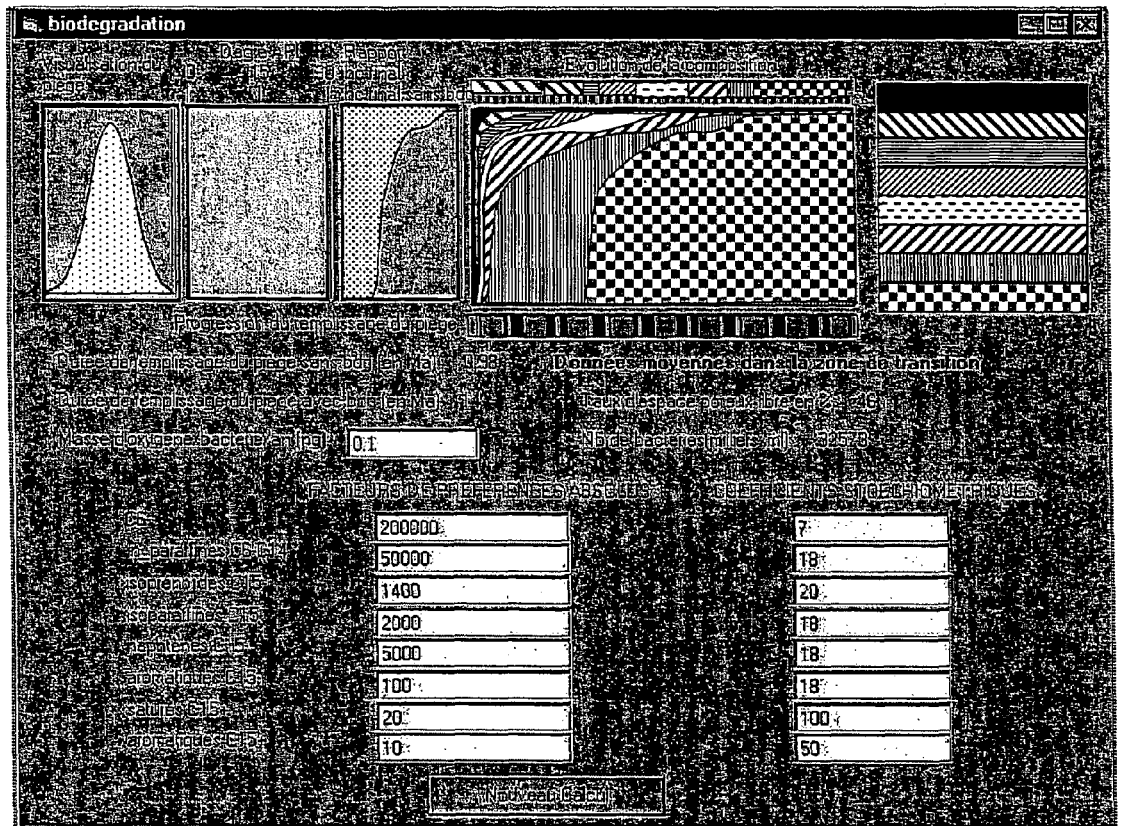
FIG. 6 shows an example of result of a calculation carried out wit the model in scenario 2 where biodegradation occurs during filling; the variation of the oil composition on the vertical of the field; connected with the geometry of the trap, can be clearly seen.

In the first scenario, illustrated by FIG. 1a, biodegradation occurs very early, from the beginning of the stage of filling of the trap by oil, because the temperature at the depth of burial of the trap lends itself to a bacterial action. The transition zone is supplied with non biodegraded oil at a regular flow rate and by water containing electron acceptors. The biodegradation front thus moves downwards as the trap is being filled. The geometry of the trap provides the bacteria with a variable filling time, which becomes increasingly long if the trap opens out. With a constant hydrocarbon flow, a biodegradation gradient will thus appear in the oil column. The oil that migrates into the trap supplies the transition zone and all of the field. Mixing between degraded and non-degraded oil takes place permanently. As can be seen in FIG. 6, the proportion of heavy oils increases with the depth.

Figure 8:
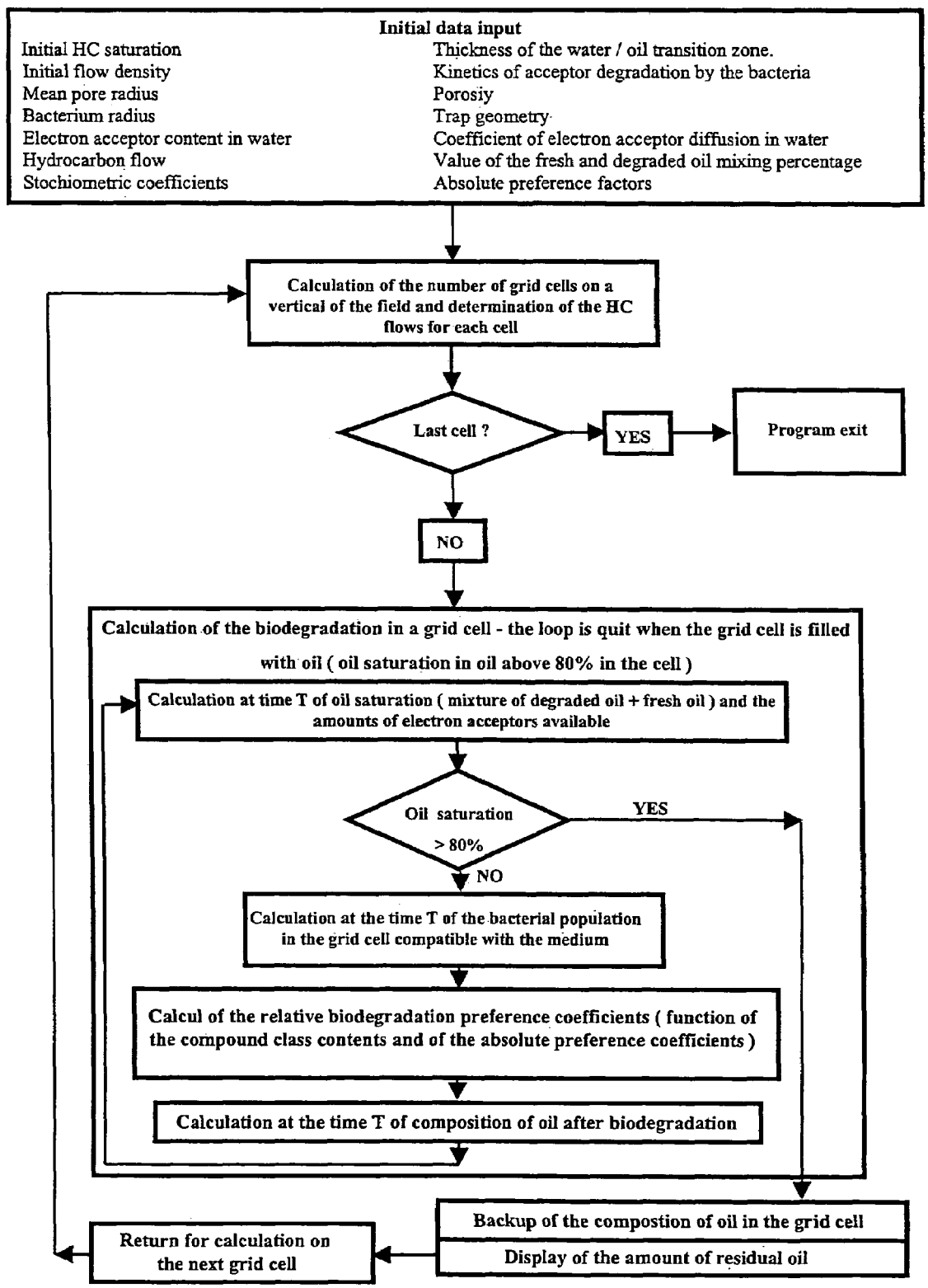
FIG. 8 shows a logic flowchart for calculation of the biodegradation on a vertical of a geologic trap according to a first biodegradation scenario.

The flowchart of FIG. 8 allows implementation of the method in its various stages according to scenario 1 as follows:

1—Input of the data required by the model.
2—Calculation, according to the geometry of the trap and of the thickness of the transition zone, of the number of grid cells corresponding to the closed height of the trap. This value is the height of the closed zone divided by the height of the transition zone. A hydrocarbon inflow is calculated for each cell, this flow corresponds to the total flow entering the reservoir divided by the total volume of the transition zone on the scale of the field (height of the transition zone*surface area of the reservoir at the depth of the cell).
3—Start of the biodegradation calculation in the first cell, this calculation is a loop which works until the porosity in the cell is filled up to 80% by oil; this calculation takes account of the values of the "fresh" hydrocarbon and electron acceptor flows entering the cell, and of the destruction of part of these hydrocarbons by the bacteria.
4—Changeover to the next grid cell located immediately below and resumption of the biodegradation calculation in this new cell, and so forth up to the last cell.
5—The progression from one grid cell to the next follows a downward direction.

Scenario 2

In the second scenario, illustrated by FIG. 1b, because of too great a depth of burial of the trap and therefore of too high a temperature, unfavorable to the bacterial activity, biodegradation has started at a late stage of filling of the trap by non biodegraded oil. The bacteria therefore attack the oil from the base of the field in the transition zone supplied by the aquifer containing electron acceptors. The consumption of oil reduces its volume in the transition zone, the oil saturation therefore decreases in this zone and, through equilibrium related to the capillary pressures, the transition zone is translated upwards, thus allowing the water and the bacteria to slowly seep through the field.

As a result the biodegradation cannot spread very deep to the top of the trap, so that an often high proportion of the oil accumulated is not degraded. This is the most favourable case wanted by operators. The proposed method allows them to select the reservoir development conditions.

Figure 9:
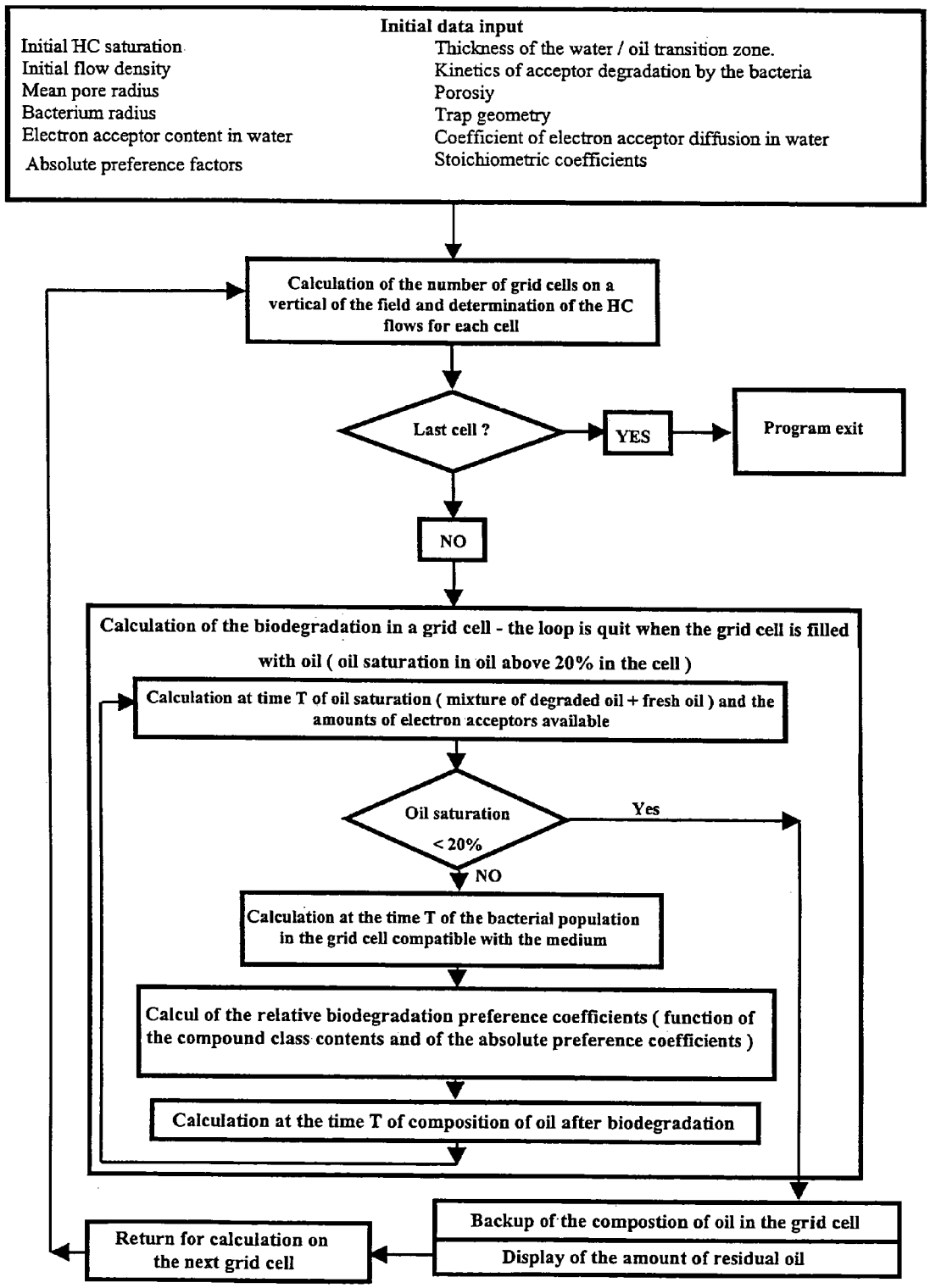
FIG. 9 shows a similar logic flowchart allowing to calculate the biodegradation on a vertical of a filled geologic trap according to a second biodegradation scenario.

The flowchart of FIG. 9 allows to implement the method in its various stages according to scenario 2. It differs from the flowchart of FIG. 8 notably in the direction of progression from cell to cell, upward here, which changes the sequences.

Selecting scenario 1 or scenario 2 for processing the prospected trap requires knowledge of its formation conditions and of its displacements, which condition the filling temperature. This selection is made from the results of a simulation carried out by means of a basin model such as Temis 2 or 3D, or of a 1D model such as Genex.

Knowing the composition of the biodegraded oil, by using a conventional thermodynamic gas-oil calculation module, the density of the oil can be calculated and the API degree of the oils in the trap as a function of the depth can be deduced there from.

Validation of the Method on Real Components

Figure 7:
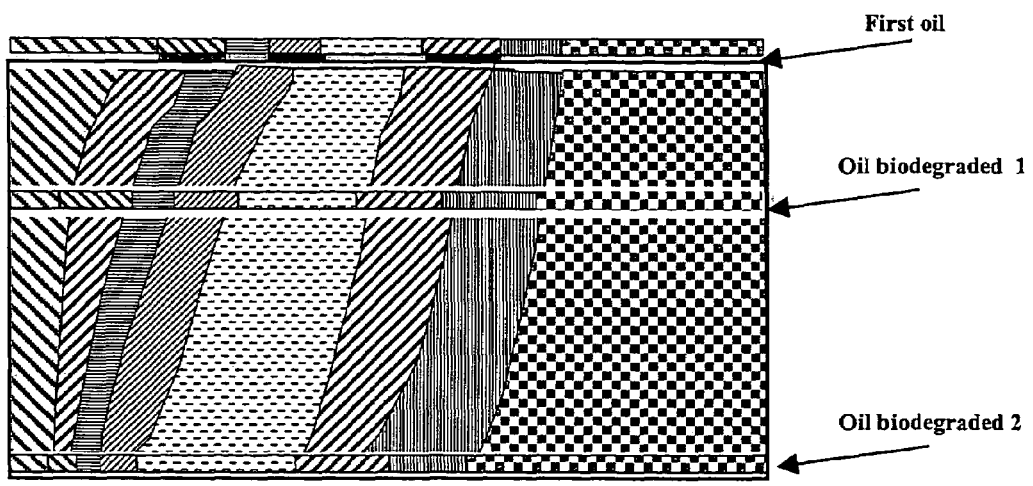
FIG. 7 shows the results of a biodegradation simulation with simulation control in relation to the compositions measured on a real case (South America—Biodegraded oil 1 and 2)

FIG. 6 shows the results of an application of the model to a trap of Gaussian form and FIG. 7 shows a real application to an oil field.

The initial fluid is an oil from a South American field. This field is biodegraded and a series of samples of variable biodegradation degrees is provided. Furthermore, biodegradation has taken place in this field by successive fits and starts, the system being regularly supplied with fresh oil pulses, sometimes degraded, sometimes not. The non biodegraded oil mixes with the earlier degraded oil.

The exercise consisted in calibrating the various preference and stoichiometric coefficients. In each grid cell, the degraded oil was mixed with non degraded oil at a constant mixing rate of 25% so as to reproduce the episodes of oil without degradation. This approach allowed to reproduce the two biodegraded samples taken into account as shown in FIG. 7.

The biodegradation model has been described in isolation using certain data obtained upstream by means of a basin model. It is clear that the software tool used to implement the method can be advantageously included as a complementary module in a basin modeling tool so as to directly get the modeling results it can provide.

The invention claimed is:

1. A method of modeling the progressive biodegradation of hydrocarbons trapped in an oil reservoir or trap studied, through action of a bacterial population in an aquifer, from data relative to the reservoir studied, concerning the form and the height of the reservoir, the physical characteristics of the porous medium, the thickness of the transition zone between the hydrocarbons and the water, the base of the transition zone containing only water and the top of the transition zone containing a residual amount of water, the composition of the hydrocarbons, the flow of electron acceptors entering the reservoir and data relative to the bacterial population in the aquifer, in order to determine the reservoir development conditions, characterised in that it comprises:
discretizing the reservoir by means of a grid wherein the height of each grid cell is the thickness of the transition zone, and
determining the variation, over the height of said reservoir, of the composition of hydrocarbons under the effect of biodegradation by iterative adjustment in each grid cell of the bacterial population to the amount of hydrocarbons available, to the pore space available, to the amount of electron acceptors present in the reservoir and to the degradation capacities of said population.

2. A method as claimed in claim 1, characterised in that the initial hydrocarbon filling rate of the reservoir when the conditions and notably the temperature prevailing in the reservoir lend themselves to biodegradation is first determined.

3. A method as claimed in claim 1, wherein the hydrocarbons have a composition comprising eight compound classes.

4. A method as claimed in claim 3, wherein the eight compound classes comprise:
1—C6–
2—N-parraffins C6-C15
3—Isoparaffins C6-C15
4—Isoprenoids C6-C15
5—Naphthenes C6-15
6—Aromatics C6-C15
7—Saturates C15+
8—Aromatics C15+

* * * * *